United States Patent
Zhang et al.

(10) Patent No.: US 10,607,135 B2
(45) Date of Patent: Mar. 31, 2020

(54) TRAINING AN AUTO-ENCODER ON A SINGLE CLASS

(71) Applicant: General Electric Company, Schenectady, NY (US)

(72) Inventors: Min Zhang, San Ramon, CA (US); Gopal Biligeri Avinash, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 261 days.

(21) Appl. No.: 15/854,980

(22) Filed: Dec. 27, 2017

(65) Prior Publication Data

US 2019/0122075 A1 Apr. 25, 2019

Related U.S. Application Data

(60) Provisional application No. 62/574,333, filed on Oct. 19, 2017.

(51) Int. Cl.
*G06N 3/04* (2006.01)
*G06N 3/08* (2006.01)
(Continued)

(52) U.S. Cl.
CPC ......... *G06N 3/0454* (2013.01); *G06K 9/6267* (2013.01); *G06N 3/08* (2013.01);
(Continued)

(58) Field of Classification Search
None
See application file for complete search history.

(56) References Cited

U.S. PATENT DOCUMENTS

| 5,769,074 A | 6/1998 | Barnhill et al. |
| 9,607,373 B2 | 3/2017 | Buisseret et al. |

(Continued)

FOREIGN PATENT DOCUMENTS

| CN | 106446895 A | * | 2/2017 |
| CN | 106952338 A | | 7/2017 |

(Continued)

OTHER PUBLICATIONS

Non-Final Office Action received for U.S. Appl. No. 15/854,971 dated Sep. 16, 2019, 27 pages.

(Continued)

*Primary Examiner* — Justin P. Misleh
(74) *Attorney, Agent, or Firm* — Amin, Turocy & Watson, LLP

(57) ABSTRACT

Systems and techniques for training an auto-encoder on a single class are presented. In one example, a system trains an auto-encoder based on first data associated with a first class to generate a trained auto-encoder. The system also applies, using a multiplier, gain data indicative of a gain value to second data associated with the first class and third data associated with a second class to generate enhanced input data that represents a differentiation between the second data associated with the first class and the third data associated with the second class. An input enhancer comprises the trained auto-encoder and the multiplier. Furthermore, the system trains a convolutional neural network based on the enhanced input data to generate a trained convolutional neural network. The system also classifies the first class and the second class based on the input enhancer and the trained convolutional neural network.

20 Claims, 10 Drawing Sheets

(51) Int. Cl.
  *G16H 30/40* (2018.01)
  *G06N 20/20* (2019.01)
  *G06K 9/62* (2006.01)
  *G06T 7/00* (2017.01)

(52) U.S. Cl.
  CPC ........... *G06N 20/20* (2019.01); *G06T 7/0012* (2013.01); *G16H 30/40* (2018.01); *G06K 2209/05* (2013.01); *G06T 2207/20081* (2013.01); *G06T 2207/20084* (2013.01)

(56) References Cited

U.S. PATENT DOCUMENTS

| | | | |
|---|---|---|---|
| 10,140,544 | B1 | 11/2018 | Zhao et al. |
| 10,192,640 | B2 | 1/2019 | Itu et al. |
| 2003/0194124 | A1 | 10/2003 | Suzuki et al. |
| 2009/0082637 | A1 | 3/2009 | Galperin |
| 2012/0051608 | A1 | 3/2012 | Avinash et al. |
| 2012/0070044 | A1 | 3/2012 | Avinash et al. |
| 2016/0300120 | A1 | 10/2016 | Haas et al. |
| 2017/0024641 | A1 | 1/2017 | Wierzynski |
| 2017/0039708 | A1 | 2/2017 | Henry et al. |
| 2017/0185871 | A1 | 6/2017 | Zhang et al. |
| 2017/0200260 | A1 | 7/2017 | Bhaskar et al. |
| 2017/0213339 | A1 | 7/2017 | Hibbard et al. |
| 2017/0270653 | A1 | 9/2017 | Garnavi et al. |
| 2017/0287134 | A1 | 10/2017 | Abedini et al. |
| 2018/0084988 | A1* | 3/2018 | Chakravorty ...... G06K 9/00617 |
| 2018/0247195 | A1 | 8/2018 | Kumar et al. |
| 2018/0253531 | A1 | 9/2018 | Sharma et al. |
| 2018/0263585 | A1 | 9/2018 | Weiss et al. |
| 2018/0315193 | A1 | 11/2018 | Paschalakis et al. |
| 2018/0350066 | A1 | 12/2018 | Zuyev et al. |
| 2018/0360313 | A1 | 12/2018 | Zhang |
| 2019/0005684 | A1 | 1/2019 | De Fauw et al. |
| 2019/0122075 | A1 | 4/2019 | Zhang et al. |
| 2019/0122360 | A1 | 4/2019 | Zhang et al. |
| 2019/0122364 | A1 | 4/2019 | Zhang et al. |

FOREIGN PATENT DOCUMENTS

| | | | |
|---|---|---|---|
| CN | 107067396 | A | 8/2017 |
| CN | 107256396 | A | 10/2017 |
| CN | 107846012 | A * | 3/2018 |
| WO | 2010/005969 | A2 | 1/2010 |

OTHER PUBLICATIONS

Hwang et al., "Self-Transfer Learning for Fully Weakly Supervised Object Localization," arXiv:1602.01625v1 [cs.CV], Feb. 4, 2016, 9 pages.

Dubost et al., "GP-Unet: Lesion Detection from Weak Labels with a 3D Regression Network", International Conference on Medical Image Computing and Computer-Assisted Intervention, MICCAI, Sep. 4, 2017, pp. 214-221.

Oktay et al., "Anatomically Constrained Neural Networks (ACNN): Application to Cardiac Image Enhancement and Segmentation", IEEE Transactions on Medical Imaging, vol. 37, No. 2, Aug. 29, 2017, pp. 1-13.

Payer et al., "Multi-Label Whole Heart Segmentation Using CNNs and Anatomical Label Configurations", Institute for Computer Graphics and Vision, vol. 10663, 2017, pp. 1-8.

Rohe et al., "Automatic Multi-Atlas Segmentation of Myocardium with SVF-Net", Statistical Atlases and Computational Models of the Heart (STACOM), Aug. 18, 2017, 9 pages.

Wang et al., "ChestX-ray8: Hospital-scale Chest X-ray Database and Benchmarks on Weakly-Supervised Classification and Localization of Common Thorax Diseases", IEEE Conference on Computer Vision and Pattern Recognition (CVPR), Jul. 21, 2017, pp. 3462-3471.

International Search Report and Written Opinion received for PCT Application Serial No. PCT/US2018/018902 dated Jul. 2, 2018, 10 pages.

Non-Final Office Action received for U.S. Appl. No. 15/792,698 dated Mar. 11, 2019, 44 pages.

International Search Report and Written Opinion received for PCT Application Serial No. PCT/US2018/031779 dated Jul. 16, 2018, 9 pages.

Shin et al., "Deep Convolutional Neural Networks for Computer-Aided Detection: CNN Architectures, Dataset Characteristics and Transfer Learning", IEEE Transactions on Medical Imaging, vol. 35, No. 5, 2016, pp. 1-14.

Zhang et al., "Deep Learning Architecture for Automated Image Feature Extraction", U.S. Appl. No. 62/574,333 dated Oct. 19, 2017, 50 pages.

Zhang et al., "Image Analysis Using Deviation From Normal Data", U.S. Appl. No. 15/855,033 dated Dec. 27, 2017, 71 pages.

Hosseini et al., "Derivative Kernels: Numerics and Applications", IEEE Transactions on Image Processing, vol. 26, No. 10, 2017, pp. 1-16.

Aljabar et al., "Multi-atlas based segmentation of brain images: Atlas selection and its effect on accuracy", NeuroImage, vol. 46, No. 3, Jul. 1, 2009, pp. 726-738.

Curiale et al., "Automatic Myocardial Segmentation by Using a Deep Deaming Network in Cardiac MRI", IEEE XLIII Latin American Computer Conference (CLEI), 2017, 6 pages.

International Search Report and Written Opinion received for PCT Application Serial No. PCT/US2018/017407 dated Jul. 4, 2018, 12 pages.

Zhang et al., "Building a Binary Neural Network Architecture", U.S. Appl. No. 15/855,015 dated Dec. 27, 2017, 76 pages.

International Search Report and Written Opinion received for PCT Application Serial No. PCT/US2018/031754 dated Aug. 16, 2018, 10 pages.

Dimitrievski et al., "High resolution depth reconstruction from monocular images and sparse point clouds using deep convolutional neural network", Proceedings of Spie, vol. 10410, 2017, pp. 1-3.

Non-Final Office Action received for U.S. Appl. No. 15/855,033 dated Aug. 21, 2019, 36 pages.

\* cited by examiner

TRAINING AN AUTO-ENCODER ON A SINGLE CLASS

RELATED APPLICATION

This application claims priority to U.S. Provisional Application No. 62/574,333, filed Oct. 19, 2017, and entitled "DEEP LEARNING ARCHITECTURE FOR AUTOMATED IMAGE FEATURE EXTRACTION", the entirety of which is incorporated herein by reference.

TECHNICAL FIELD

This disclosure relates generally to artificial intelligence.

BACKGROUND

Artificial Intelligence (AI) can be employed for classification and/or analysis of digital images. For instance, AI can be employed for image recognition. In certain technical applications, AI can be employed to enhance imaging analysis. In an example, region-of-interest based deep neural networks can be employed to localize a feature in a digital image. However, accuracy and/or efficiency of a classification and/or an analysis of digital images using conventional artificial techniques is generally difficult to achieve. Furthermore, conventional artificial techniques for classification and/or analysis of digital images generally requires labor-intensive processes such as, for example, pixel annotations, voxel level annotations, etc. As such, conventional artificial techniques for classification and/or analysis of digital images can be improved.

SUMMARY

The following presents a simplified summary of the specification in order to provide a basic understanding of some aspects of the specification. This summary is not an extensive overview of the specification. It is intended to neither identify key or critical elements of the specification, nor delineate any scope of the particular implementations of the specification or any scope of the claims. Its sole purpose is to present some concepts of the specification in a simplified form as a prelude to the more detailed description that is presented later.

According to an embodiment, a system includes an auto-encoder component, a multiplier component, a convolutional neural network component, and a classification component. The auto-encoder component trains an auto-encoder based on first data associated with a first class to generate a trained auto-encoder. The multiplier component applies, using a multiplier, gain data indicative of a gain value to second data associated with the first class and second data associated with a second class to generate enhanced input data that represents a differentiation between the second data associated with the first class and the third data associated with the second class. An input enhancer comprises the trained auto-encoder and the multiplier. The convolutional neural network component that trains a convolutional neural network based on the enhanced input data to generate a trained convolutional neural network. The classification component classifies the first class and the second class based on the input enhancer and the trained convolutional neural network.

According to another embodiment, a method is provided. The method provides for using a processor operatively coupled to memory to execute computer executable components to perform acts such as inputting first image data associated with a first class. The method also provides for acts such as training an auto-encoder based on the first class associated with the first image data to generate a trained auto-encoder. The method also provides for acts such as inputting second image data associated with a first class and third image data associated with a second class to the trained auto-encoder. Furthermore, the method provides for acts such as applying, using a multiplier, gain data indicative of a gain value to the second image data and the third image data to generate enhanced input data that represents a differentiation between the second image data associated with the first class and the third image data associated with the second class, wherein an input enhancer comprises the trained auto-encoder and the multiplier. The method also provides for acts such as training a convolutional neural network based on the enhanced input data to generate a trained convolutional neural network. Additionally, the method provides for acts such as identifying the first class and the second class from new image data based on the input enhancer and the trained convolutional neural network.

According to yet another embodiment, a computer readable storage device comprising instructions that, in response to execution, cause a system comprising a processor to perform operations, comprising: training an auto-encoder based on first image data associated with a first class to generate a trained auto-encoder, applying, using a multiplier, gain data indicative of a gain value to second image data associated with the first class and third image data associated with a second class to generate enhanced input data that represents a differentiation between the second image data associated with the first class and the third image data associated with the second class, training a convolutional neural network based on the enhanced input data to generate a trained convolutional neural network, and identifying the first class and the second class from new image data based on an input enhancer and the trained convolutional neural network. The input enhancer comprises the trained auto-encoder and the multiplier.

The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, implementations, objects and advantages of the present invention will be apparent upon consideration of the following detailed description, taken in conjunction with the accompanying drawings, in which like reference characters refer to like parts throughout, and in which.

DETAILED DESCRIPTION

Figure 1:
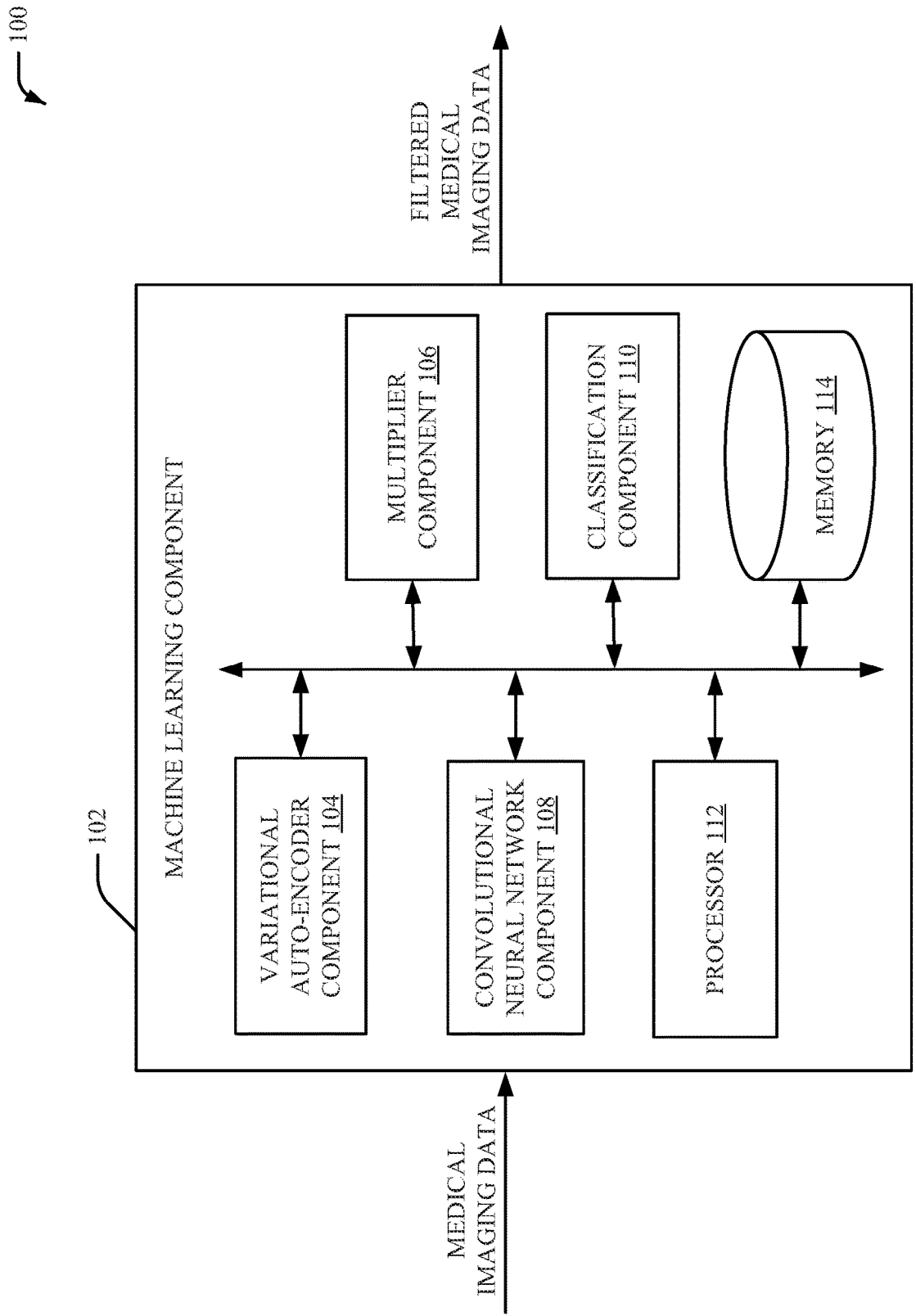
FIG. 1 illustrates a high-level block diagram of an example machine learning component, in accordance with various aspects and implementations described herein.

Various aspects of this disclosure are now described with reference to the drawings, wherein like reference numerals are used to refer to like elements throughout. In the following description, for purposes of explanation, numerous specific details are set forth in order to provide a thorough understanding of one or more aspects. It should be understood, however, that certain aspects of this disclosure may be practiced without these specific details, or with other methods, components, materials, etc. In other instances, well-known structures and devices are shown in block diagram form to facilitate describing one or more aspects.

Systems and techniques for training an auto-encoder on a single class are presented. For example, as compared to conventional artificial intelligence (AI) techniques, the subject innovations provide for a novel AI framework that employs a trained auto-encoder associated with a one class classifier. In an embodiment, an auto-encoder can be trained on a single class to generate a trained auto-encoder. The auto-encoder can be, for example, a variational auto-encoder. Furthermore, first data associated with a first class can be input to the trained auto-encoder. In an example, the first data can be first image data (e.g., first medical imaging data). A multiplier can be employed to add a gain to second data associated with the first class and third data associated with the second classes to generate an enhanced input representing a differentiation between the first class and the second classes. The second data can be second image data (e.g., second medical imaging data) that is different than the first data. Furthermore, the third data can be third image data (e.g., third medical imaging data) that is different than the first data. In an aspect, an input enhancer can include the trained auto-encoder and the multiplier to facilitate generation of the enhanced input. Additionally, a convolutional neural network (CNN) can be trained based on the enhanced input to generate a trained CNN. The input enhancer and the trained CNN can be employed to classify the first class and the second class. Additionally or alternatively, the input enhancer and the trained CNN can be employed to identify a subset of data from the second data that is not associated with the first class and/or a subset of data from the third data that is not associated with the second class. For example, the input enhancer and the trained CNN can be employed to identify one or more outliers (e.g., one or more outlier images) from the first class and/or the second class. In certain embodiments, the subset of data (e.g., the one or more outliers) can be filtered from the second data and/or the third data to generate filtered data (e.g., filtered image data). Furthermore, in an embodiment, the filtered data can be employed by a machine learning model for classification, localization and/or analysis of one or more features within the filtered data. As such, by employing the novel AI framework as described herein, detection and/or localization of one or more features associated with digital images (e.g., detection and/or localization of one or more diseases for a patient associated with medical imaging data) can be improved. Furthermore, accuracy and/or efficiency for classification and/or analysis of digital images (e.g., medical imaging data) can be improved. Moreover, effectiveness of a machine learning model for classification and/or analysis of digital images (e.g., medical imaging data) can be improved, performance of one or more processors that execute a machine learning model for classification and/or analysis of digital images (e.g., medical imaging data) can be improved, and/or efficiency of one or more processors that execute a machine learning model for classification and/or analysis of digital images (e.g., medical imaging data) can be improved.

Referring initially to FIG. 1, there is illustrated an example system 100 for training an auto-encoder on a single class, according to an aspect of the subject disclosure. The system 100 can be employed by various systems, such as, but not limited to medical device systems, medical imaging systems, medical diagnostic systems, medical systems, medical modeling systems, enterprise imaging solution systems, advanced diagnostic tool systems, simulation systems, image management platform systems, care delivery management systems, artificial intelligence systems, machine learning systems, neural network systems, modeling systems, aviation systems, power systems, distributed power systems, energy management systems, thermal management systems, transportation systems, oil and gas systems, mechanical systems, machine systems, device systems, cloud-based systems, heating systems, HVAC systems, medical systems, automobile systems, aircraft systems, water craft systems, water filtration systems, cooling systems, pump systems, engine systems, prognostics systems, machine design systems, and the like. In one example, the system 100 can be associated with a classification system to facilitate visualization and/or interpretation of medical imaging data. Moreover, the system 100 and/or the components of the system 100 can be employed to use hardware and/or software to solve problems that are highly technical in nature (e.g., related to processing digital data, related to processing medical imaging data, related to medical modeling, related to medical imaging, related to artificial intelligence, etc.), that are not abstract and that cannot be performed as a set of mental acts by a human.

The system 100 can include a machine learning component 102 that can include an auto-encoder component 104, a multiplier component 106, a convolutional neural network component 108, and a classification component 110. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. The system 100 (e.g., the machine learning component 102) can include memory 114 for storing computer executable components and instructions. The system 100 (e.g., the machine learning component 102) can further include a processor 112 to facilitate operation of the instructions (e.g., computer executable components and instructions) by the system 100 (e.g., the machine learning component 102).

The machine learning component 102 (e.g., the auto-encoder component 104) can receive medical imaging data (e.g., MEDICAL IMAGING DATA shown in FIG. 1). The medical imaging data can be two-dimensional medical imaging data and/or three-dimensional medical imaging data generated by one or more medical imaging devices. For instance, the medical imaging data can be electromagnetic radiation imagery captured via a set of sensors (e.g., a set of sensors associated with a medical imaging device). In certain embodiments, the medical imaging data can be a series of electromagnetic radiation imagery captured via a set of sensors (e.g., a set of sensors associated with a medical imaging device) during an interval of time. The medical imaging data can be received directly from one or more medical imaging devices. Alternatively, the medical imaging data can be stored in one or more databases that receives and/or stores the medical imaging data associated with the one or more medical imaging devices. A medical imaging device can be, for example, an x-ray device, a computed tomography (CT) device, another type of medical imaging device, etc.

The auto-encoder component 104 can train an auto-encoder based on a first portion of the medical imaging data. For example, the auto-encoder component 104 can train an auto-encoder based on first data from the medical imaging data that is associated with a first class. In an embodiment, the auto-encoder can be a variational auto-encoder. Based on the first portion of the medical imaging data (e.g., based on the first data from the medical imaging data that is associated with the first class), the auto-encoder component 104 can generate a trained auto-encoder. Additionally, the auto-encoder component 104 can generate a reconstructed first portion of the medical imaging data (e.g., reconstructed first data) based on the first portion of the medical imaging data (e.g., based on the first data from the medical imaging data that is associated with the first class). In an embodiment, the auto-encoder component 104 can compare the reconstructed first portion of the medical imaging data (e.g., reconstructed first data) to the first portion of the medical imaging data (e.g., the first data from the medical imaging data that is associated with the first class) to determine loss function data. The loss function data can be indicative of a loss function for the auto-encoder. Furthermore, the auto-encoder component 104 can generate the trained auto-encoder based on the loss function data. In an aspect, the auto-encoder component 104 can compare the reconstructed first portion of the medical imaging data (e.g., reconstructed first data) to the first portion of the medical imaging data (e.g., the first data from the medical imaging data that is associated with the first class) to minimize the loss function data. For example, the auto-encoder component 104 can train the auto-encoder until the loss function data satisfies a defined value.

The multiplier component 106 can apply gain data indicative of a gain value to a second portion of the medical imaging data and a third portion of the medical imaging data. The second portion of the medical imaging data can be, for example, second data from the medical imaging data that is associated with the first class. Furthermore, the third portion of the medical imaging data can be, for example, third data from the medical imaging data that is associated with a second class. In an aspect, the first class can be a first category classification (e.g., a first type of medical image, a first type of medical image associated with a first anatomical region, etc.) for the medical imaging data and the second class can be a second category classification (e.g., a second type of medical image, a second type of medical image associated with a first anatomical region, etc.) for the medical imaging data. In an aspect, the multiplier component 106 can apply the gain data to the second portion of the medical imaging data (e.g., the second data associated with the first class) and the third portion of the medical imaging data (e.g., the third data associated with the second class) to generate enhanced input data. The enhanced input data can represent a differentiation between the second portion of the medical imaging data (e.g., the second data associated with the first class) and the third portion of the medical imaging data (e.g., the third data associated with the second class). In another aspect, the multiplier component 106 can employ a multiplier to apply the gain data to the second portion of the medical imaging data (e.g., the second data associated with the first class) and the third portion of the medical imaging data (e.g., the third data associated with the second class). In an embodiment, an input enhancer in communication with the system 100 (e.g., the machine learning component 102) can include the trained auto-encoder and the multiplier. In certain embodiments, the input enhancer can include the system 100 (e.g., the machine learning component 102).

The convolutional neural network component 108 can perform a machine learning process (e.g., an artificial intelligence process for machine learning) based on the enhanced input data. In an aspect, the convolutional neural network component 108 can train a convolutional neural network based on the enhanced input data to generate a trained convolutional neural network. The convolutional neural network can be, for example, a spring network of convolutional layers. For instance, the convolutional neural network can perform a plurality of sequential and/or parallel downsampling and upsampling of the enhanced input data associated with convolutional layers of the convolutional neural network. In an example, the convolutional neural network component 108 can perform a first convolutional layer process associated with sequential downsampling of the enhanced input data and a second convolutional layer process associated with sequential upsampling of the enhanced input data. The spring network of convolutional layers can include the first convolutional layer process associated with the sequential downsampling and the second convolutional layer process associated with sequential upsampling. The spring network of convolutional layers employed by the convolutional neural network component 108 can alter convolutional layer filters similar to functionality of a spring. For instance, the convolutional neural network component 108 can analyze the enhanced input data based on a first convolutional layer filter that comprises a first size, a second convolutional layer filter that comprises a second size that is different than the first size, and a third convolutional layer filter that comprises the first size associated with the first convolutional layer filter.

The classification component 110 can classify the first class and the second class based on the input enhancer and the trained convolutional neural network. For example, the classification component 110 can determine a main classification for a new portion of the medical imaging data (e.g., new data of the medical imaging data that is associated with the first class and/or the second class). Additionally or alternatively, the classification component 110 can identify a subset of data from the new portion of the medical imaging data that is not associated with the first class and/or a subset of data from the new portion of the medical imaging data that is not associated with the second class based on the input enhancer and the trained convolutional neural network. For instance, the subset of data can be outlier data that is associated with a class that is different than the first class and/or that is different than the second class. Furthermore, the classification component 110 can generate filtered medical imaging data (e.g., FILTERED MEDICAL IMAGING DATA shown in FIG. 1). The filtered medical imaging data can be medical imaging data without the subset of data from the first portion of the medical imaging data. For example, the filtered medical imaging data can be a filtered version of the medical imaging data that does not include the outlier data that is associated with the class that is different than the first class and/or that is different than the second class. In certain embodiments, the classification component 110 can determine a classification for the new portion of the medical imaging data (e.g., the new data from the medical imaging data) based on the input enhancer and the trained convolutional neural network. For example, the classification component 110 can extract information that is indicative of correlations, inferences and/or expressions from the new portion of the medical imaging data (e.g., the new data from the medical imaging data). In an aspect, the classification component 110 can perform learning with respect to the new portion of the medical imaging data (e.g., the new data from the medical imaging data) explicitly or implicitly. The classification component 110 can also employ an automatic classification system and/or an automatic classification process to facilitate analysis of the new portion of the medical imaging data (e.g., the new data from the medical imaging data). For example, the classification component 110 can employ a probabilistic and/or statistical-based analysis (e.g., factoring into the analysis utilities and costs) to learn and/or generate inferences with respect to the new portion of the medical imaging data (e.g., the new data from the medical imaging data). The classification component 110 can employ, for example, a support vector machine (SVM) classifier to learn and/or generate inferences for the new portion of the medical imaging data (e.g., the new data from the medical imaging data). Additionally or alternatively, the classification component 110 can employ other classification techniques associated with Bayesian networks, decision trees and/or probabilistic classification models. Classifiers employed by the classification component 110 can be explicitly trained (e.g., via a generic training data) as well as implicitly trained (e.g., via receiving extrinsic information). For example, with respect to SVM's, SVM's can be configured via a learning or training phase within a classifier constructor and feature selection module. A classifier can be a function that maps an input attribute vector, x=(x1, x2, x3, x4, xn), to a confidence that the input belongs to a class—that is, f(x)=confidence(class).

In an embodiment, the first portion of the medical imaging data (e.g., the first data from the medical imaging data that is associated with the first class) can be a first set of images associated with the first class. The auto-encoder component 104 can train the auto-encoder based on the first set of images associated with the first class to generate a reconstructed first set of images. Furthermore, the second portion of the medical imaging data (e.g., the second data from the medical imaging data that is associated with the first class) can be a second set of images associated with the first class. Moreover, the third portion of the medical imaging data (e.g., the third data from the medical imaging data that is associated with the second class) can be a third set of images associated with the second class. The multiplier component 106 can apply the gain data to the second set of images and the third set of images to generate the enhanced input data. The convolutional neural network component 108 can also train the convolutional neural network based on the enhanced input data associated with the second set of images and the third set of images to generate a trained convolutional neural network. Additionally, the classification component 110 can classify the first class and the second class from a new set of images based on the input enhancer and the trained convolutional neural network. Additionally, in certain embodiments, the classification component 110 can identify one or more outlier images from a new set of images based on the input enhancer and the trained convolutional neural network. In certain embodiments, the auto-encoder component 104 can compare reconstructed second data and reconstructed third data to the second data and the third data to determine loss function data indicative of a loss function for the auto-encoder. Furthermore, the auto-encoder component 104 can generate the trained auto-encoder based on the loss function data.

It is to be appreciated that technical features of the machine learning component 102 are highly technical in nature and not abstract ideas. Processing threads of the machine learning component 102 that process and/or analyze the medical imaging data, determine outlier medical imaging data, etc. cannot be performed by a human (e.g., are greater than the capability of a single human mind). For example, the amount of the medical imaging data processed, the speed of processing of the medical imaging data and/or the data types of the medical imaging data processed by the machine learning component 102 over a certain period of time can be respectively greater, faster and different than the amount, speed and data type that can be processed by a single human mind over the same period of time. Furthermore, the medical imaging data processed by the machine learning component 102 can be one or more medical images generated by sensors of a medical imaging device. Moreover, the machine learning component 102 can be fully operational towards performing one or more other functions (e.g., fully powered on, fully executed, etc.) while also processing the medical imaging data.

Figure 2:
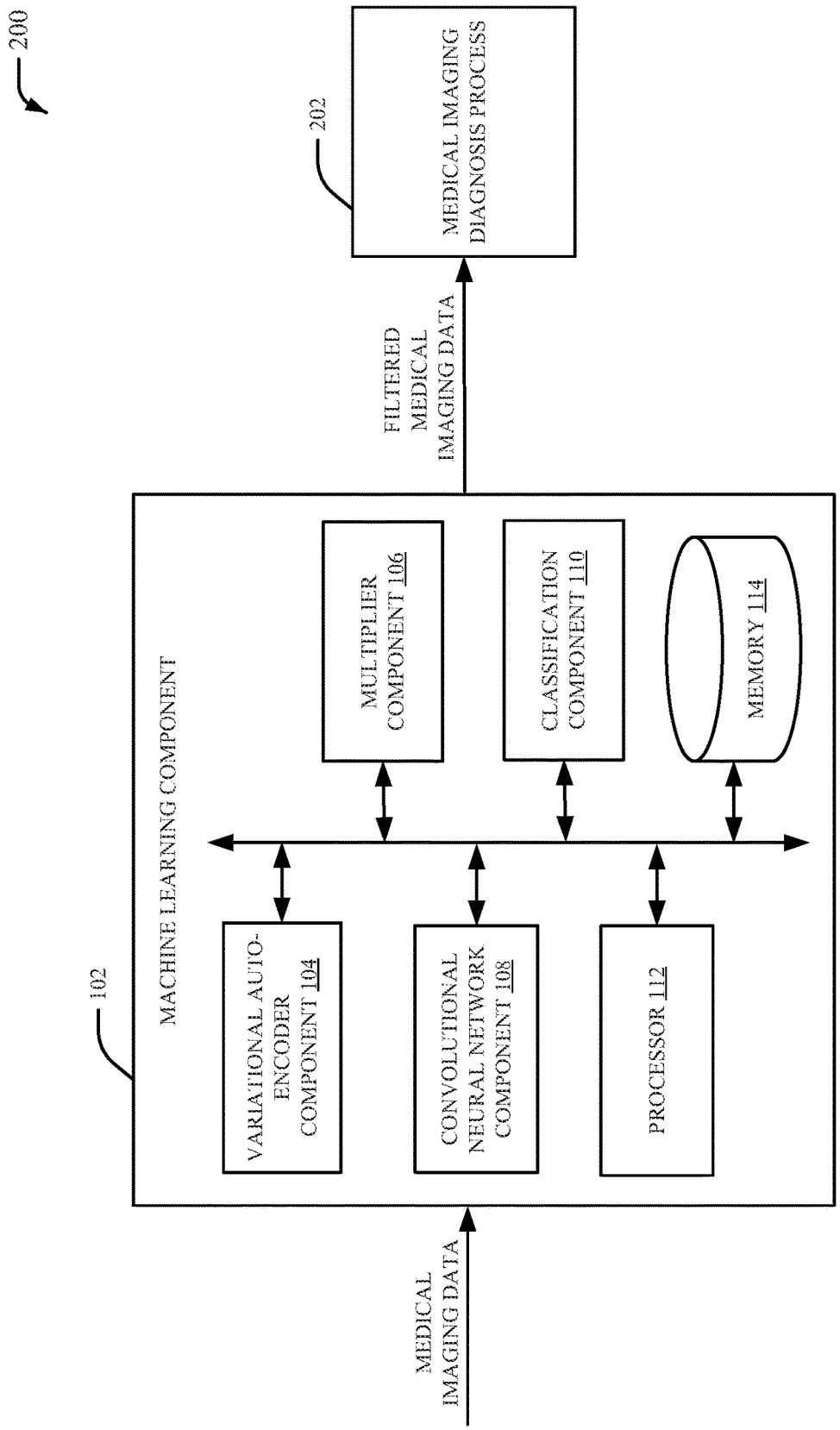
FIG. 2 illustrates a system that includes an example machine learning component and an example medical imaging data artificial intelligence model, in accordance with various aspects and implementations described herein.

Referring now to FIG. 2, there is illustrated a non-limiting implementation of a system 200 in accordance with various aspects and implementations of this disclosure. Repetitive description of like elements employed in other embodiments described herein is omitted for sake of brevity.

The system 200 includes the machine learning component 102 and medical imaging diagnosis process 202. The machine learning component 102 can include the auto-encoder component 104, the multiplier component 106, the convolutional neural network component 108, the classification component 110, the processor 112 and/or the memory 114. The machine learning component 102 can provide the filtered medical imaging data to the medical imaging diagnosis process 202. In an aspect, the medical imaging diagnosis process 202 can perform deep learning to facilitate classification and/or localization of one or more diseases associated with the filtered medical imaging data. In another aspect, the medical imaging diagnosis process 202 can perform deep learning based on a convolutional neural network that receives the filtered medical imaging data. A disease classified and/or localized by the medical imaging diagnosis process 202 can include, for example, a lung disease, a heart disease, a tissue disease, a bone disease, a tumor, a cancer, tuberculosis, cardiomegaly, hypoinflation of a lung, opacity of a lung, hyperdistension, a spine degenerative disease, calcinosis, or another type of disease associated with an anatomical region of a patient body. In an aspect, the medical imaging diagnosis process 202 can determine a prediction for a disease associated with the filtered medical imaging data. For example, the medical imaging diagnosis process 202 can determine a probability score for a disease associated with the filtered medical imaging data (e.g., a first percentage value representing likelihood of a negative prognosis for the disease and a second value representing a likelihood of a positive prognosis for the disease).

Figure 3:
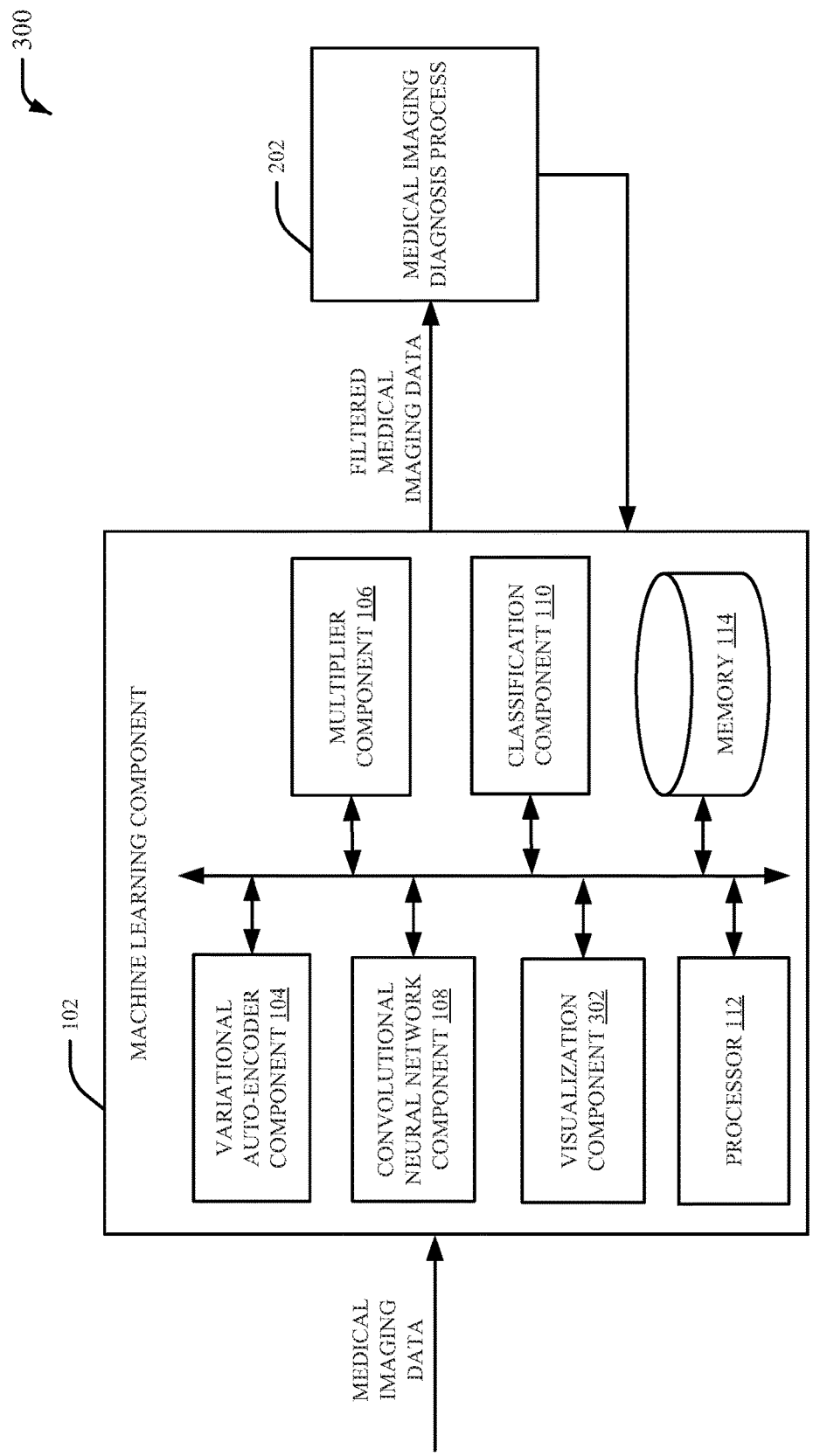
FIG. 3 illustrates a high-level block diagram of another example machine learning component, in accordance with various aspects and implementations described herein.

Referring now to FIG. 3, there is illustrated a non-limiting implementation of a system 300 in accordance with various aspects and implementations of this disclosure. Repetitive description of like elements employed in other embodiments described herein is omitted for sake of brevity.

The system 300 includes the machine learning component 102. The machine learning component 102 can include the auto-encoder component 104, the multiplier component 106, the convolutional neural network component 108, the classification component 110, the processor 112, the memory 114 and/or a visualization component 302. In an embodiment, the system 300 can further include the medical imaging diagnosis process 202. The visualization component 302 can generate a human-interpretable visualization of the subset of data (e.g., the outlier data) from the second portion of the medical imaging data and/or the third portion of the medical imaging data. Additionally or alternatively, visualization component 302 can generate a human-interpretable visualization of the filtered medical imaging data. In an embodiment, the visualization component 302 can generate a multi-dimensional visualization associated with the classification for the second portion of the medical imaging data (e.g., the second data from the medical imaging data that is associated with the first class) and/or the classification for the third portion of the medical imaging data (e.g., the third data from the medical imaging data that is associated with the second class). In another embodiment, the visualization component 302 can generate deep learning data based on a classification and/or a localization for a portion of an anatomical region associated with the filtered medical imaging data. The deep learning data can include, for example, a classification and/or a location for one or more diseases located in the filtered medical imaging data. In certain embodiments, the deep learning data can include probability data indicative of a probability for one or more diseases being located in the filtered medical imaging data. The probability data can be, for example, a probability array of data values for one or more diseases being located in the filtered medical imaging data. Additionally or alternatively, the visualization component 302 can generate a multi-dimensional visualization associated with classification and/or localization for a portion of an anatomical region associated with the filtered medical imaging data.

The multi-dimensional visualization can be a graphical representation of the filtered medical imaging data that shows a classification and/or a location of one or more diseases with respect to a patient body. The visualization component 302 can also generate a display of the multi-dimensional visualization of the diagnosis provided by the medical imaging diagnosis process 202. For example, the visualization component 302 can render a 2D visualization of a portion of an anatomical region on a user interface associated with a display of a user device such as, but not limited to, a computing device, a computer, a desktop computer, a laptop computer, a monitor device, a smart device, a smart phone, a mobile device, a handheld device, a tablet, a portable computing device or another type of user device associated with a display. In an aspect, the multi-dimensional visualization can include deep learning data. In another aspect, the deep learning data can also be rendered on the 3D model as one or more dynamic visual elements. The visualization component 302 can, in an embodiment, alter visual characteristics (e.g., color, size, hues, shading, etc.) of at least a portion of the deep learning data associated with the multi-dimensional visualization based on the classification and/or the localization for the portion of the anatomical region. For example, the classification and/or the localization for the portion of the anatomical region can be presented as different visual characteristics (e.g., colors, sizes, hues or shades, etc.), based on a result of deep learning and/or medical imaging diagnosis by the medical imaging diagnosis process 202. In another aspect, the visualization component 302 can allow a user to zoom into or out with respect to the deep learning data associated with the multi-dimensional visualization. For example, the visualization component 302 can allow a user to zoom into or out with respect to a classification and/or a location of one or more diseases identified in the anatomical region of the patient body. As such, a user can view, analyze and/or interact with the deep learning data associated with the multi-dimensional visualization for the filtered medical imaging data.

Figure 4:
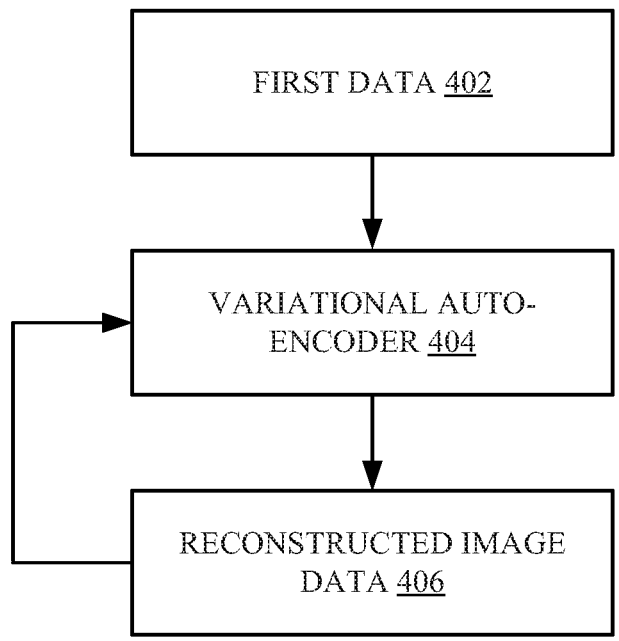
FIG. 4 illustrates an example system associated with a training phase for an auto-encoder, in accordance with various aspects and implementations described herein.

Referring now to FIG. 4, there is illustrated a non-limiting implementation of a system 400 in accordance with various aspects and implementations of this disclosure. Repetitive description of like elements employed in other embodiments described herein is omitted for sake of brevity.

The system 400 includes first data 402, an auto-encoder 404 and reconstructed image data 406. The first data 402 can be associated with a first class. Furthermore, the first data 402 can correspond to, for example, the first portion of the medical imaging data (e.g., the first data from the medical imaging data that is associated with the first class). In an embodiment, the auto-encoder 404 can be included in the auto-encoder component 104. In another embodiment, the auto-encoder 404 can be in communication with the auto-encoder component 104. In yet another embodiment, the auto-encoder 404 can be a variational auto encoder. The auto-encoder 404 can be trained on a single class to generate a trained version of the auto-encoder 404. In an aspect, the auto-encoder 404 can receive the first data 402. The first data 402 can be associated with a single class of data. For example, the first data 402 can include a set of medical images associated with a first classification (e.g., a set of chest medical images, etc.). Furthermore, the auto-encoder 404 can be trained based on the first data 402. Based on the first data 402, the auto-encoder 404 can generate the reconstructed image data 406. In another aspect, the auto-encoder 404 can include an encoder and a decoder. The encoder of the auto-encoder 404 can generate a compressed version of the reconstructed image data 406. The decoder of the auto-encoder 404 can learn to reconstruct the first data 402 during training of the auto-encoder 404 based on the compressed version of the reconstructed image data 406. Furthermore, in an embodiment, the auto-encoder 404 can compare the reconstructed image data 406 to the first data 402 to determine loss function data indicative of a loss function for the auto-encoder 404. A length of a training phase for the auto-encoder 404 can be determined based on the loss function data. For example, the auto-encoder 404 can be trained until the loss function data for the auto-encoder 404 satisfied a defined criterion.

Figure 5:
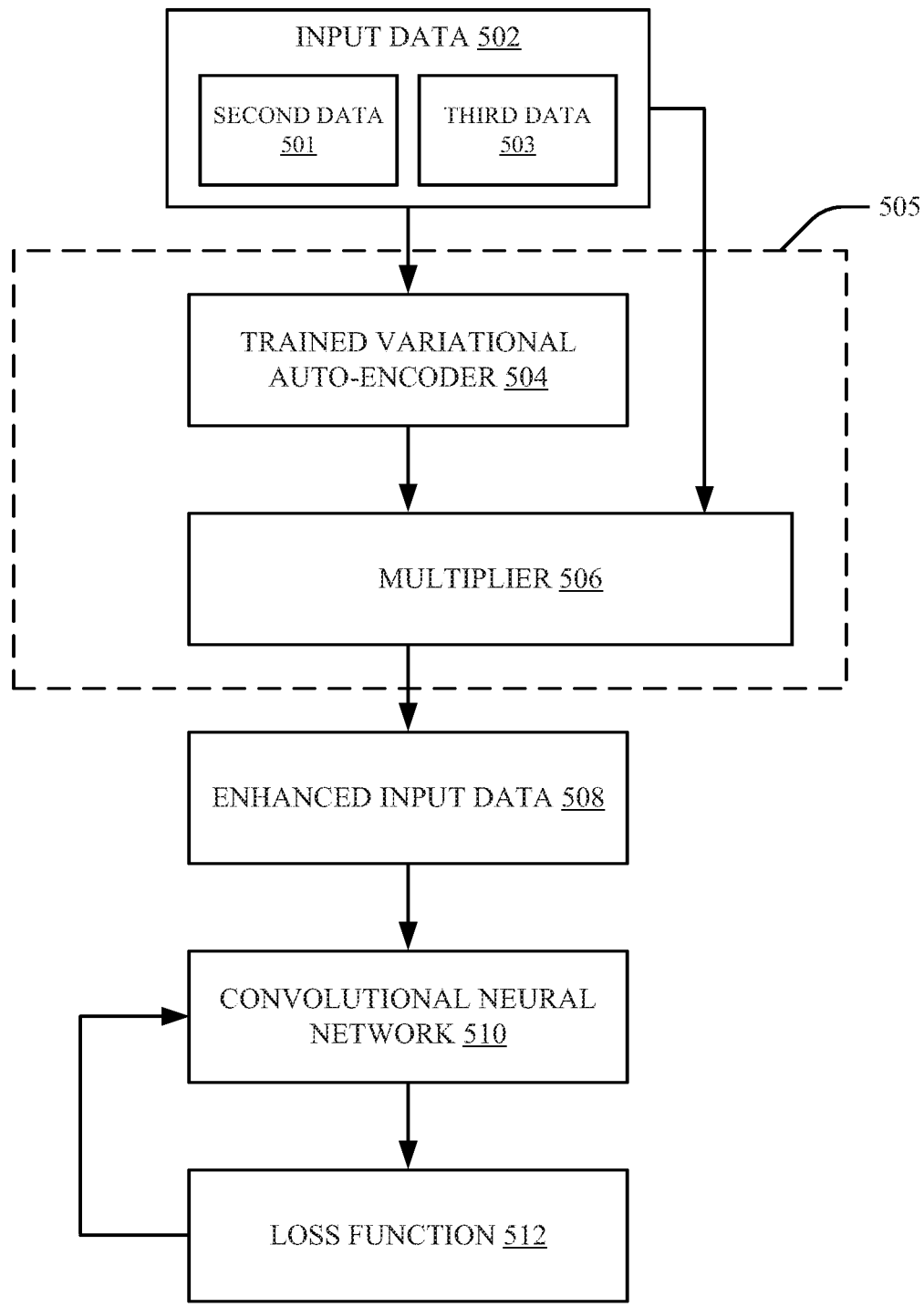
FIG. 5 illustrates an example system associated with a training phase for a convolutional neural network, in accordance with various aspects and implementations described herein.

Referring now to FIG. 5, there is illustrated a non-limiting implementation of a system 500 in accordance with various aspects and implementations of this disclosure. Repetitive description of like elements employed in other embodiments described herein is omitted for sake of brevity.

The system 500 includes input data 502, a trained auto-encoder 504 and a multiplier 506. The trained auto-encoder 504 can be, for example, a trained version of the auto-encoder 404. In an embodiment, the multiplier 506 can be included in the multiplier component 106. In another embodiment, the multiplier 506 can be in communication with the multiplier component 106. The system 500 can be associated with a training mode (e.g., a training phase) for a convolutional neural network. Input data 502 can include, for example, second data 501 associated with the first class and third data 503 associated with a second class. The second data 501 can be second image data (e.g., second medical imaging data) and the third data 503 can be third image data (e.g., third imaging data). For instance, the second data 501 can correspond to, for example, the second portion of the medical imaging data (e.g., the second data from the medical imaging data that is associated with the first class). Furthermore, the third data 503 can correspond to, for example, the third portion of the medical imaging data (e.g., the third data from the medical imaging data that is associated with the second class). In certain embodiments, the second data 501 associated with the first class from the input data 502 and/or the third data 503 associated with the second class from the input data 502 can be provided to the trained auto-encoder 504. The trained auto-encoder 504 can generate reconstructed second data associated with the first class and/or reconstructed third data associate with the second class. In an embodiment, the second data 501 associated with the first class and the third data 503 associated with the second class can be provided to the multiplier 506. The multiplier 506 can apply gain data indicative of a gain value to the second data 501 associated with the first class and the third data 503 associated with the second class to generate enhanced input data 508. The enhanced input data 508 can represent a differentiation between the second data 501 associated with the first class in the input data 502 and the third data 503 associated with the second class in the input data 502. In an embodiment, an input enhancer 505 can include the trained auto-encoder 504 and the multiplier 506. Furthermore, a convolutional neural network 510 can be trained based on the enhanced input data 508 to generate a trained convolutional neural network. In an aspect, a length of a training phase for the convolutional neural network 510 can be determined based on the loss function 512. For example, the convolutional neural network 510 can be trained until the loss function 512 satisfied a defined criterion.

Figure 6:
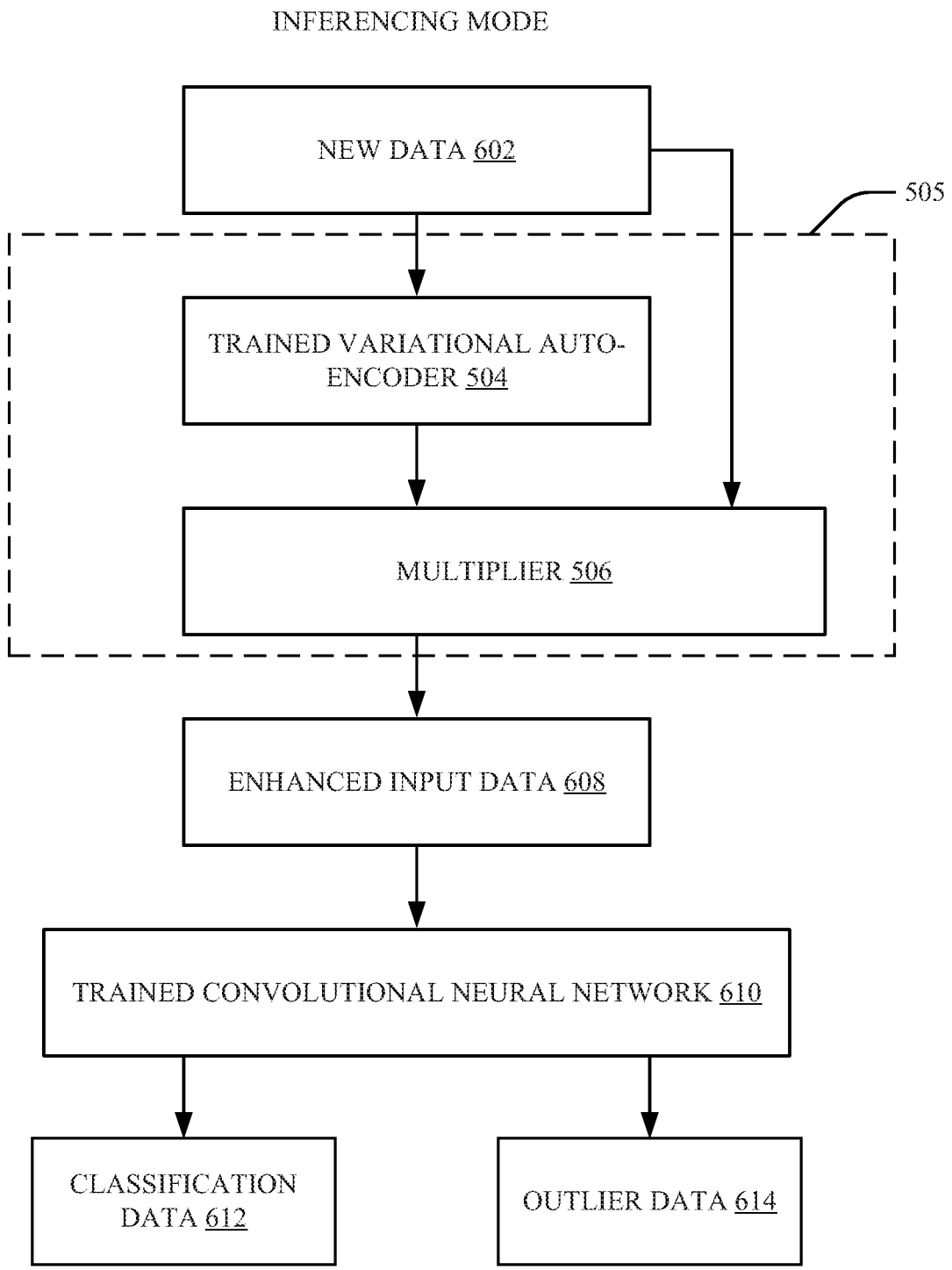
FIG. 6 illustrates an example system associated with an inference phase for a convolutional neural network, in accordance with various aspects and implementations described herein.

Referring now to FIG. 6, there is illustrated a non-limiting implementation of a system 600 in accordance with various aspects and implementations of this disclosure. Repetitive description of like elements employed in other embodiments described herein is omitted for sake of brevity.

The system 600 includes the input enhancer 505 that includes the trained auto-encoder 604 and the multiplier 606. The system 600 includes a trained convolutional neural network 610. In an embodiment, the trained convolutional neural network 610 can be a trained version of the convolutional neural network 510. The system 600 can be associated with an inferencing mode (e.g., an inferencing phase) for a convolutional neural network. New data 602 can include, for example, image data (e.g., medical imaging data) to be analyzed. In an embodiment, the new data 602 can include, for example, new data associated with a first class and new data associated with a second class. In another embodiment, the new data 602 can be provided to the trained auto-encoder 504. The trained auto-encoder 504 can generate reconstructed new data. In yet another embodiment, the new data 602 can be provided to the multiplier 506. The multiplier 506 can apply gain data indicative of a gain value to the new data 602. For example, the multiplier 506 can apply gain data indicative of a gain value to the new data associated with the first class and the new data associated with the second class to generate enhanced input data 608. The enhanced input data 608 can represent a differentiation between the new data associated with the first class and the new data associated with the second class. Furthermore, the trained convolutional neural network 610 generate classification data 612 and/or outlier data 614 based on the enhanced input data 608. The classification data 612 can be, for example, a classification for the first class from the new data 602 (e.g., a main classification for the new data 602). The outlier data 614 can be a classification for the second class from the new data 602. In an aspect, the outlier data 614 can be a subset of data from the new data 602 that is associated with the second class. For example, the outlier data 614 can be data associated with the second class that is different than the first class for the first data (e.g., different than the first class associated with the classification data 612).

Figure 7:
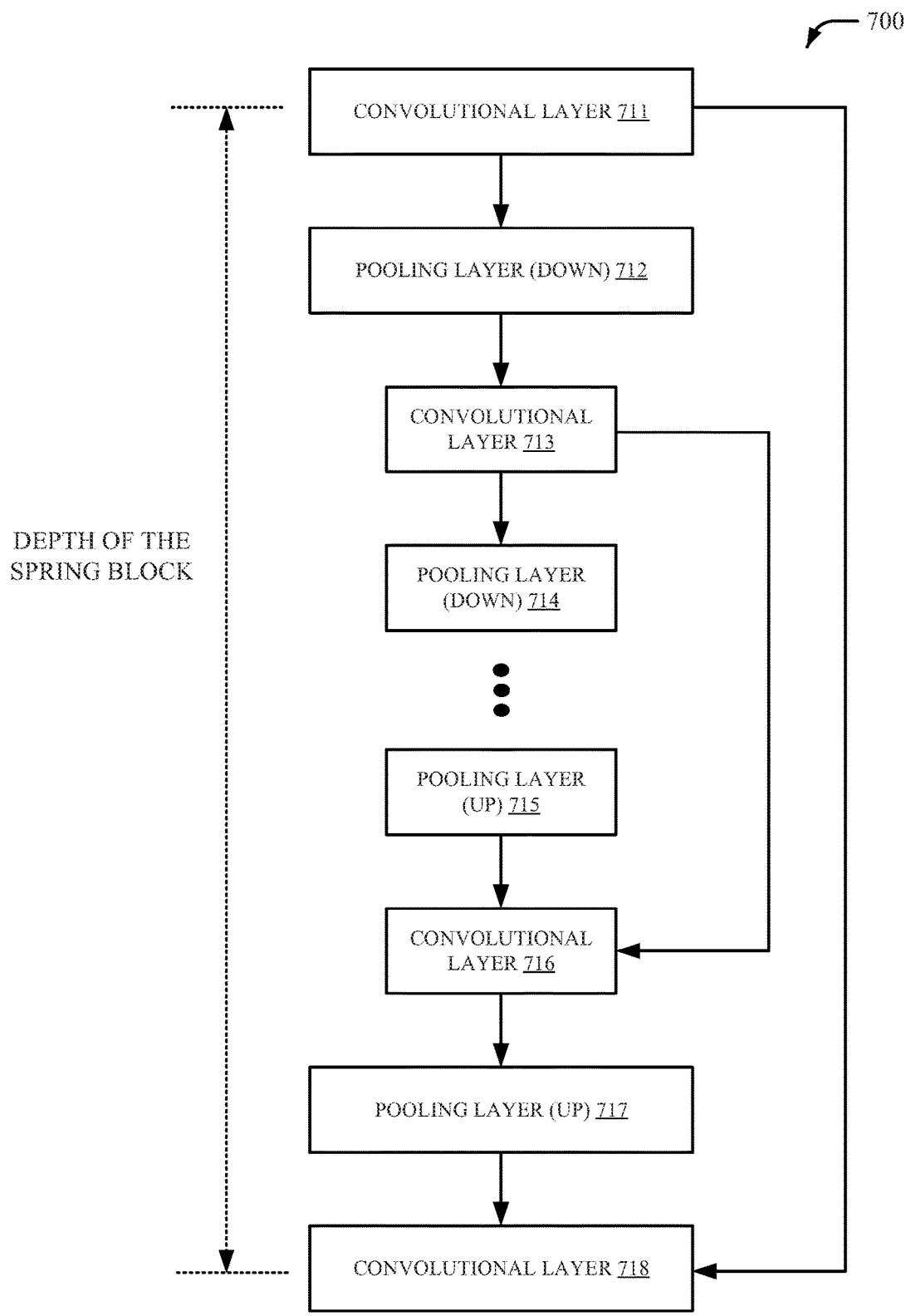
FIG. 7 illustrates a high-level block diagram of an example spring block associated with a convolutional neural network, in accordance with various aspects and implementations described herein.

Referring now to FIG. 7, there is illustrated a non-limiting implementation of a system 700 in accordance with various aspects and implementations of this disclosure. The system 700 can illustrate an example spring block for a deep learning architecture associated with a convolutional neural network. For example, the system 700 can correspond to a convolutional neural network employed by the convolutional neural network component 108. In another example, the system 700 can correspond to the convolutional neural network 510 and/or the trained convolutional neural network 610. The spring block associated with the system 700 can be associated with sequential upsampling and downsampling for a spring deep learning network. In an aspect, the spring block associated with the system 700 can consist of connected pair down sampling/up sampling layers and convolutional layers. The spring block associated with the system 700 can also be very flexible in terms of depth (e.g., number of paired up/down sampling convolutional layers) and/or size of convolutional filters (e.g. a convolutional filter size equal to 3×3, a convolutional filter size equal to 5×5, a convolutional filter size equal to 7×7, etc.).

In an embodiment, the system 700 can include a convolutional layer 711. The convolutional layer 711 can be a first convolutional layer of a convolutional neural network that processes imaging data. Furthermore, the convolutional layer 711 can be associated with a first filter size. The convolutional layer 711 can be followed by a pooling layer (down) 712. The pooling layer (down) 712 can be associated with downsampling. For instance, the pooling layer (down) 712 can reduce dimensionality of data generated by the convolutional layer 711. In one example, the pooling layer (down) 712 can reduce dimensionality of a feature map for imaging data processed by the convolutional layer 711. The pooling layer (down) 712 can be followed by a convolutional layer 713. The convolutional layer 713 can be a second convolutional layer of the convolutional neural network that processes the imaging data. Furthermore, the convolutional layer 713 can be associated with a second filter size that is different than the first filter size associated with the convolutional layer 711. For example, the second filter size associated with the convolutional layer 713 can be smaller than the first filter size associated with the convolutional layer 711. The convolutional layer 713 can be followed by a pooling layer (down) 714. The pooling layer (down) 714 can be associated with downsampling. For instance, the pooling layer (down) 714 can reduce dimensionality of data generated by the convolutional layer 713. In one example, the pooling layer (down) 714 can reduce dimensionality of a feature map for imaging data processed by the convolutional layer 713. The pooling layer (down) 714 can be followed by a convolutional layer (not shown), which, in turn, can be followed by a pooling layer (up) 715. However, in certain embodiments, the pooling layer (down) 714 can be followed by one or more other convolutional layers and/or one or more other pooling layers (down) prior to the pooling layer (up) 715 to further process imaging data with different filter sizes and/or further reduction to dimensionality of data. The pooling layer (up) 715 can be associated with upsampling. For instance, the pooling layer (up) 715 can increase dimensionality of data generated by one or more convolutional layers. In one example, the pooling layer (up) 715 can increase dimensionality of a feature map for imaging data processed by one or more convolutional layers. The pooling layer (up) 715 can be followed by a convolutional layer 716. The convolutional layer 716 can be, for example, a third convolutional layer of the convolutional neural network that processes the imaging data. Furthermore, the convolutional layer 716 can be associated with the second filter size associated with the convolutional layer 713.

The convolutional layer 716 can be followed by a pooling layer (up) 717. The pooling layer (up) 717 can be associated with upsampling. For instance, the pooling layer (up) 717 can increase dimensionality of data generated by the convolutional layer 716. In one example, the pooling layer (up) 717 can increase dimensionality of a feature map for imaging data processed by the convolutional layer 716. The pooling layer (up) 717 can be followed by a convolutional layer 718. The convolutional layer 718 can be, for example, a fourth convolutional layer of the convolutional neural network that processes the imaging data. Furthermore, the convolutional layer 718 can be associated with the first filter size associated with the convolutional layer 716. As such, the spring block associated with the system 700 can behave similar to functionality of a spring where a filter size for one or more convolutional layers are repeated while processing imaging data via a convolutional neural network.

Figure 8:
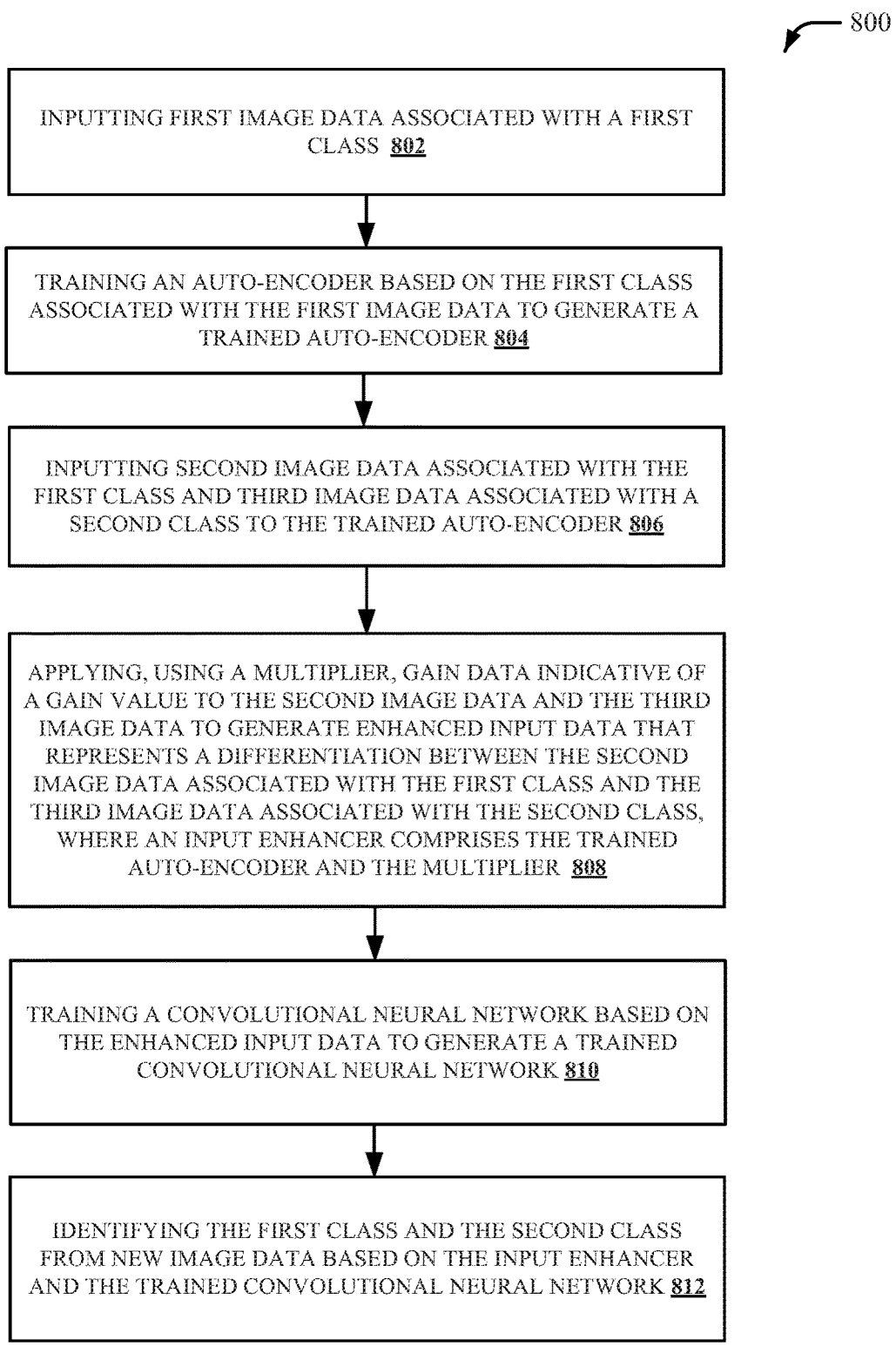
FIG. 8 depicts a flow diagram of an example method for training an auto-encoder on a single class, in accordance with various aspects and implementations described herein.

FIG. 8 illustrates a methodology and/or a flow diagram in accordance with the disclosed subject matter. For simplicity of explanation, the methodology is depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodology in accordance with the disclosed subject matter. In addition, those skilled in the art will understand and appreciate that the methodology could alternatively be represented as a series of interrelated states via a state diagram or events. Additionally, it should be further appreciated that methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device or storage media.

Referring to FIG. 8, there is illustrated a non-limiting implementation of a methodology 800 for training an auto-encoder on a single class, according to an aspect of the subject innovation. At 802, first image data associated with a first class is inputted (e.g., by auto-encoder component 104). In an embodiment, the first image data can include medical imaging data such as, for example, electromagnetic radiation imagery, one or more x-ray images, one or more CT scan images, another type of medical imagery, etc. In another embodiment, the first image data can be electromagnetic radiation imagery captured via a set of sensors (e.g., a set of sensors associated with a medical imaging device).

At 804, an auto-encoder is trained (e.g., by auto-encoder component 104) based on the first class associated with the first image data to generate a trained auto-encoder. In one example, the auto-encoder can be a variational auto-encoder. In an aspect, the auto-encoder can generate reconstructed image data based on the first class of the first image data. Furthermore, the auto-encoder can include an encoder and a decoder to facilitate training of the auto-encoder. For example, the encoder of the auto-encoder can generate a compressed version of the reconstructed image data. The decoder of the auto-encoder can learn to reconstruct the image data during training of the auto-encoder based on the compressed version of the reconstructed image data. In an embodiment, the auto-encoder can compare the reconstructed image data to an original version of the first image data to determine loss function data indicative of a loss function for the auto-encoder. A length of a training phase for the auto-encoder can be determined based on the loss function data. For example, the auto-encoder can be trained until the loss function data for the auto-encoder satisfied a defined criterion.

At 806, second image data associated with the first class and third image data associated with a second class is input (e.g., by auto-encoder component 104) to the trained auto-encoder. For example, the second image data associated with the first class can be provided to the trained auto-encoder to generate reconstructed second image data associated with the first class. Additionally or alternatively, the third image data associated with the second class can be provided to the trained auto-encoder to generate reconstructed third image data associated with the second class. In an embodiment, the second image data can include medical imaging data such as, for example, electromagnetic radiation imagery, one or more x-ray images, one or more CT scan images, another type of medical imagery, etc. Furthermore, the third image data can include medical imaging data such as, for example, electromagnetic radiation imagery, one or more x-ray images, one or more CT scan images, another type of medical imagery, etc. In another embodiment, the second image data and/or the third image data can be electromagnetic radiation imagery captured via a set of sensors (e.g., a set of sensors associated with a medical imaging device).

At 808, gain data indicative of a gain value is applied, using a multiplier (e.g., by multiplier component 106), to the second image data and the third image data to generate enhanced input data that represents a differentiation between the second image data associated with the first class and the third image data associated with the second class. The input enhancer comprises the trained auto-encoder and the multiplier. In an aspect, the multiplier and the gain data can be employed to provide improved clarity with respect to a difference between the second image data and the third image data. In one example, the gain data can be applied to the reconstructed second image data and the reconstructed third image data to generate the enhanced input data.

At 810, a convolutional neural network is trained (e.g., by convolutional neural network component 108) based on the enhanced input data to generate a trained convolutional neural network. The convolutional neural network can be, for example, a spring network of convolutional layers. For instance, the convolutional neural network can perform a plurality of sequential and/or parallel downsampling and upsampling of the enhanced input data associated with convolutional layers of the convolutional neural network. The convolutional neural network can provide a first convolutional layer process associated with sequential downsampling of the enhanced input data and a second convolutional layer process associated with sequential upsampling of the enhanced input data. The spring network of convolutional layers can include the first convolutional layer process associated with the sequential downsampling and the second convolutional layer process associated with sequential upsampling. The spring network of convolutional layers associated with the convolutional neural network can alter convolutional layer filters similar to functionality of a spring. For instance, the convolutional neural network can analyze the enhanced input data based on a first convolutional layer filter that comprises a first size, a second convolutional layer filter that comprises a second size that is different than the first size, and a third convolutional layer filter that comprises the first size associated with the first convolutional layer filter.

At 812, the first class and the second class from new image data are identified (e.g., by classification component 110) based on the input enhancer and the trained convolutional neural network. In certain embodiments, a subset of image data from the new data can be identified based on the input enhancer and the trained convolutional neural network. For instance, the subset of image data can include one or more outlier images that satisfy a defined criterion from the new data. In one example, the subset of image data can include one or more outlier images that are associated with a class that is different than the first class and/or the second class. In certain embodiments, the methodology 800 can further include determining a classification for the new image data based on the input enhancer and the trained convolutional neural network. In certain embodiments, the methodology 800 can additionally include generating a multi-dimensional visualization associated with the classification for the new image data. The new image data can include medical imaging data such as, for example, electromagnetic radiation imagery, one or more x-ray images, one or more CT scan images, another type of medical imagery, etc. In an embodiment, the new image data can be electromagnetic radiation imagery captured via a set of sensors (e.g., a set of sensors associated with a medical imaging device).

The aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 9:
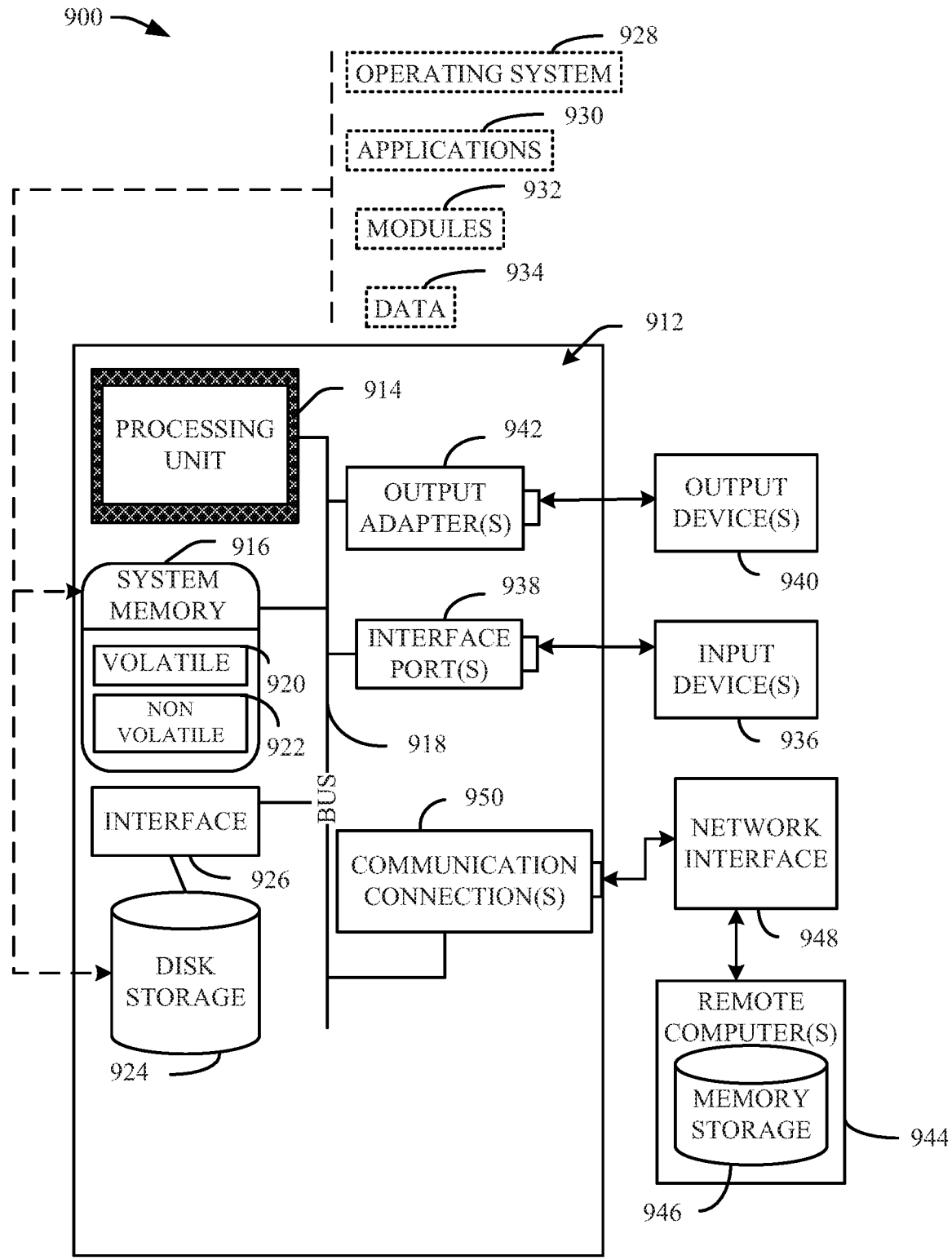
FIG. 9 is a schematic block diagram illustrating a suitable operating environment.
Figure 10:
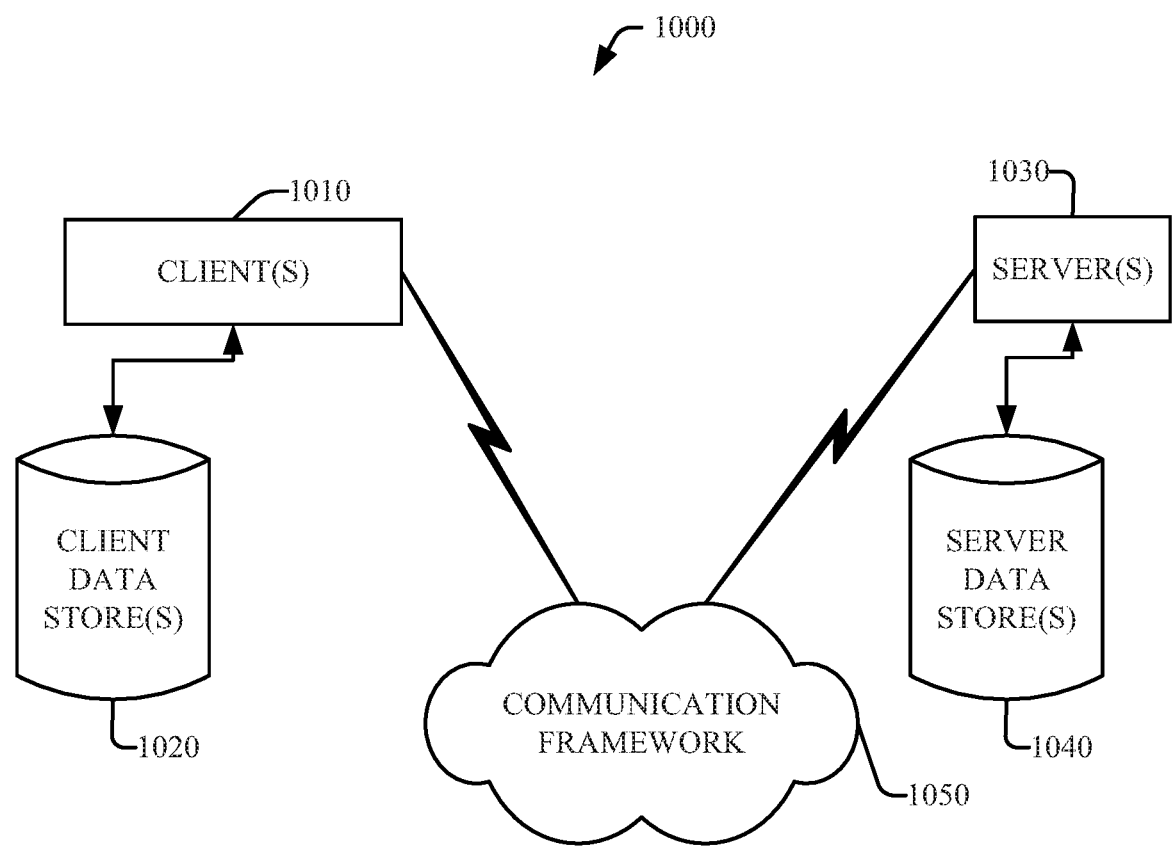
FIG. 10 is a schematic block diagram of a sample-computing environment.

In order to provide a context for the various aspects of the disclosed subject matter, FIGS. 9 and 10 as well as the following discussion are intended to provide a brief, general description of a suitable environment in which the various aspects of the disclosed subject matter may be implemented.

With reference to FIG. 9, a suitable environment 900 for implementing various aspects of this disclosure includes a computer 912. The computer 912 includes a processing unit 914, a system memory 916, and a system bus 918. The system bus 918 couples system components including, but not limited to, the system memory 916 to the processing unit 914. The processing unit 914 can be any of various available processors. Dual microprocessors and other multiprocessor architectures also can be employed as the processing unit 914.

The system bus 918 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 916 includes volatile memory 920 and nonvolatile memory 922. The basic input/output system (BIOS), containing the basic routines to transfer information between elements within the computer 912, such as during start-up, is stored in nonvolatile memory 922. By way of illustration, and not limitation, nonvolatile memory 922 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 920 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 912 also includes removable/non-removable, volatile/non-volatile computer storage media. FIG. 9 illustrates, for example, a disk storage 924. Disk storage 924 includes, but is not limited to, devices like a magnetic disk drive, floppy disk drive, tape drive, Jaz drive, Zip drive, LS-100 drive, flash memory card, or memory stick. The disk storage 924 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 924 to the system bus 918, a removable or non-removable interface is typically used, such as interface 926.

FIG. 9 also depicts software that acts as an intermediary between users and the basic computer resources described in the suitable operating environment 900. Such software includes, for example, an operating system 928. Operating system 928, which can be stored on disk storage 924, acts to control and allocate resources of the computer system 912. System applications 930 take advantage of the management of resources by operating system 928 through program modules 932 and program data 934, e.g., stored either in system memory 916 or on disk storage 924. It is to be appreciated that this disclosure can be implemented with various operating systems or combinations of operating systems.

A user enters commands or information into the computer 912 through input device(s) 936. Input devices 936 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 914 through the system bus 918 via interface port(s) 938. Interface port(s) 938 include, for example, a serial port, a parallel port, a game port, and a universal serial bus (USB). Output device(s) 940 use some of the same type of ports as input device(s) 936. Thus, for example, a USB port may be used to provide input to computer 912, and to output information from computer 912 to an output device 940. Output adapter 942 is provided to illustrate that there are some output devices 940 like monitors, speakers, and printers, among other output devices 940, which require special adapters. The output adapters 942 include, by way of illustration and not limitation, video and sound cards that provide a means of connection between the output device 940 and the system bus 918. It should be noted that other devices and/or systems of devices provide both input and output capabilities such as remote computer(s) 944.

Computer 912 can operate in a networked environment using logical connections to one or more remote computers, such as remote computer(s) 944. The remote computer(s) 944 can be a personal computer, a server, a router, a network PC, a workstation, a microprocessor based appliance, a peer device or other common network node and the like, and typically includes many or all of the elements described relative to computer 912. For purposes of brevity, only a memory storage device 946 is illustrated with remote computer(s) 944. Remote computer(s) 944 is logically connected to computer 912 through a network interface 948 and then physically connected via communication connection 950. Network interface 948 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 950 refers to the hardware/software employed to connect the network interface 948 to the bus 918. While communication connection 950 is shown for illustrative clarity inside computer 912, it can also be external to computer 912. The hardware/software necessary for connection to the network interface 948 includes, for exemplary purposes only, internal and external technologies such as, modems including regular telephone grade modems, cable modems and DSL modems, ISDN adapters, and Ethernet cards.

FIG. 10 is a schematic block diagram of a sample-computing environment 1000 with which the subject matter of this disclosure can interact. The system 1000 includes one or more client(s) 1010. The client(s) 1010 can be hardware and/or software (e.g., threads, processes, computing devices). The system 1000 also includes one or more server(s) 1030. Thus, system 1000 can correspond to a two-tier client server model or a multi-tier model (e.g., client, middle tier server, data server), amongst other models. The server(s) 1030 can also be hardware and/or software (e.g., threads, processes, computing devices). The servers 1030 can house threads to perform transformations by employing this disclosure, for example. One possible communication between a client 1010 and a server 1030 may be in the form of a data packet transmitted between two or more computer processes.

The system 1000 includes a communication framework 1050 that can be employed to facilitate communications between the client(s) 1010 and the server(s) 1030. The client(s) 1010 are operatively connected to one or more client data store(s) 1020 that can be employed to store information local to the client(s) 1010. Similarly, the server(s) 1030 are operatively connected to one or more server data store(s) 1040 that can be employed to store information local to the servers 1030.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A machine learning system, comprising:
a memory that stores computer executable components;
a processor that executes the computer executable components stored in the memory, wherein the computer executable components comprise:
an auto-encoder component that trains an auto-encoder based on first data associated with a first class to generate a trained auto-encoder;
a multiplier component that applies, using a multiplier, gain data indicative of a gain value to second data associated with the first class and third data associated with a second class to generate enhanced input data that represents a differentiation between the second data associated with the first class and the third data associated with the second class, wherein an input enhancer comprises the trained auto-encoder and the multiplier;
a convolutional neural network component that trains a convolutional neural network based on the enhanced input data to generate a trained convolutional neural network; and
a classification component that classifies the first class and the second class based on the input enhancer and the trained convolutional neural network.

2. The machine learning system of claim 1, wherein the first data is a first set of images associated with the first class, and wherein the auto-encoder component trains the auto-encoder based on the first set of images associated with the first class.

3. The machine learning system of claim 2, wherein the second data is a second set of images associated with the first class and the third data is a third set of images associated with the second class, and wherein the multiplier component that applies the gain data to the second set of images and the third set of images to generate the enhanced input data.

4. The machine learning system of claim 2, wherein the classification component classifies the first class and the second class from a new set of images based on the input enhancer and the trained convolutional neural network.

5. The machine learning system of claim 1, wherein the auto-encoder component compares reconstructed second data and reconstructed third data to the second data and the third data to determine loss function data indicative of a loss function for the auto-encoder, and wherein the auto-encoder component generates the trained auto-encoder based on the loss function data.

6. The machine learning system of claim 1, wherein the convolutional neural network performs a plurality of sequential and/or parallel downsampling and upsampling of the enhanced input data associated with convolutional layers of the convolutional neural network.

7. The machine learning system of claim 1, wherein the classification component determines a classification for new data associated with the first class and the second class based on the input enhancer and the trained convolutional neural network.

8. The machine learning system of claim 7, wherein the computer executable components further comprise:
a visualization component that generates a multi-dimensional visualization associated with the classification for the new data.

9. A method, comprising using a processor operatively coupled to memory to execute computer executable components to perform the following acts:
inputting first image data associated with a first class;
training an auto-encoder based on the first class associated with the first image data to generate a trained auto-encoder;
inputting second image data associated with the first class and third image data associated with a second class to the trained auto-encoder;
applying, using a multiplier, gain data indicative of a gain value to the second image data and the third image data to generate enhanced input data that represents a differentiation between the second image data associated with the first class and the third image data associated with the second class, wherein an input enhancer comprises the trained auto-encoder and the multiplier;
training a convolutional neural network based on the enhanced input data to generate a trained convolutional neural network; and
identifying the first class and the second class from new image data based on the input enhancer and the trained convolutional neural network.

10. The method of claim 9, wherein the training the auto-encoder comprises training the auto-encoder based on the first image data associated with the first class to generate reconstructed first image data.

11. The method of claim 10, wherein the training the auto-encoder comprises comparing the reconstructed first image data to the first image data to determine loss function data indicative of a loss function for the auto-encoder.

12. The method of claim 11, wherein the training the auto-encoder comprises generating the trained auto-encoder based on the loss function data.

13. The method of claim 9, wherein the applying the gain data comprises applying the gain data to reconstructed second image data and reconstructed third image data to generate the enhanced input data.

14. The method of claim 9, wherein the identifying comprises identifying one or more outlier images that satisfy a defined criterion from the first class based on the input enhancer and the trained convolutional neural network.

15. The method of claim 9, wherein the training the convolutional neural network comprises performing a plurality of sequential and/or parallel downsampling and upsampling of the enhanced input data associated with convolutional layers of the convolutional neural network.

16. The method of claim 9, further comprising:
determining a classification for the first class and the second class from new data based on the input enhancer and the trained convolutional neural network.

17. The method of claim 16, further comprising:
generating a multi-dimensional visualization associated with the classification for the new data.

18. A computer readable storage device comprising instructions that, in response to execution, cause a system comprising a processor to perform operations, comprising:
training an auto-encoder based on first image data associated with a first class to generate a trained auto-encoder;
applying, using a multiplier, gain data indicative of a gain value to second image data associated with the first class and third image data associated with a second class to generate enhanced input data that represents a differentiation between the second image data associated with the first class and the third image data associated with the second class, wherein an input enhancer comprises the trained auto-encoder and the multiplier;

training a convolutional neural network based on the enhanced input data to generate a trained convolutional neural network; and identifying the first class and the second class from new image data based on the input enhancer and the trained convolutional neural network.

19. The computer readable storage device of claim 18, wherein the identifying comprises identifying one or more outlier images from the first class based on the input enhancer and the trained convolutional neural network.

20. The computer readable storage device of claim 18, wherein the training the auto-encoder comprises comparing reconstructed first image data to the first image data to minimize loss function data indicative of a loss function for the auto-encoder.

* * * * *